(12) United States Patent
Wider

(10) Patent No.: US 6,500,861 B1
(45) Date of Patent: Dec. 31, 2002

(54) ANTIMICROBIAL COMPOSITION AND METHODS OF USE IN THE TREATMENT OF DISEASE

(76) Inventor: Michael D. Wider, 8 Hanover, Pleasant Ridge, MI (US) 48069

( * ) Notice: Subject to any disclaimer, the term of this patent is extended or adjusted under 35 U.S.C. 154(b) by 0 days.

(21) Appl. No.: 09/644,333

(22) Filed: Aug. 23, 2000

(51) Int. Cl.$^7$ .................. A61K 31/22; A61K 31/225; A61K 31/20
(52) U.S. Cl. .................. 514/546; 514/547; 514/557; 514/558; 514/560
(58) Field of Search ................ 514/546, 547, 514/557, 558, 560

(56) References Cited

U.S. PATENT DOCUMENTS 6,071,961 A * 6/2000 Wider .................. 514/557

FOREIGN PATENT DOCUMENTS

WO 9719593 * 6/1997

* cited by examiner

*Primary Examiner*—Kevin E. Weddington
(74) *Attorney, Agent, or Firm*—Plunkett & Cooney, P.C.; Arnold S. Weintraub, Esq

(57) ABSTRACT

A composition for eliminating an infection in a body space or cavity or on the epidermis of the body of the user is formed from an antimicrobial active agent which is, preferably, a fatty acid or mixture of fatty acids, an organic acid and a hydrotroper solubilizer. This composition in concentrate form can be diluted or admixed with the deionized, pyrogen-free water to form an effective use solution. The active ingredients herein are either UPS or food grade components.

20 Claims, No Drawings

ANTIMICROBIAL COMPOSITION AND METHODS OF USE IN THE TREATMENT OF DISEASE

BACKGROUND OF THE INVENTION

1. Field of the Invention.

The present invention relates to the use biocidal compositions of matter to eliminate infections from various body cavities. More particularly, the present invention concerns the use of biocidal compositions for eliminating infections in the thoracic cavity, abdominal cavity, synovial spaces, urinary bladder, lungs, sinus cavities, external auditory canal, oral pharynx, pericardial space, and the like by microorganisms and viruses. Even more particularly, the present invention concerns the elimination of infections including pathogenic microorganisms including Gram negative and positive bacteria, yeast, fungi, rickettsia and the like as well as normally nonpathogenic microorganisms present in the body cavities or spaces, which spaces or cavities do not normally harbor or support the growth of such organisms.

2. Prior Art

It is recognized and well documented that microorganisms present in the internal spaces and tissues of the body can cause disease i.e. infection, leading to physical debility of the animal or person and may even cause death. Today, typically, microorganism infection is normally treated with antibiotics. Antibiotics are made from compounds that interfere with the normal growth and proliferation of microorganisms. The action of these antibiotics involves specific interference with cell wall synthesis, protein synthesis or the like in the bacteria as they attempt to proliferate. There are analogous compounds prescribed for the treatment of fungal and yeast infections. There are a limited number of medications that interfere with the proliferation or viruses and viral particles in host cells preventing disease or discomfort normally caused by the virus.

Antibiotics normally act by interfering with biochemical mechanisms internal to the microorganism. Antibiotics are used as topical creams but are primarily administered either orally or in injectable form. The antibiotic then circulates through the blood stream and permeates the infected tissue where it comes in contact with the infecting organisms.

It is widely recognized by medical practitioners that the use of antibiotics has several problems and limitations that can lead to unwanted side effects or ineffective action against the infecting organisms. It is also recognized that any one antibiotic is effective against a limited spectrum of microorganisms and that this limited action frequently requires the medical practitioner to evaluate the effectiveness of the antibiotic in vitro prior to use which test is referred to in medical practice as a culture and sensitivity assay. The use of an antibiotic that is not active against the specific microorganism involved in the infection will not eliminate the infection and can actually accelerate growth of the organism by eliminating competing organisms leading to further progress of the resulting disease.

On the other hand testing for effectiveness of an antibiotic can delay treatment and result in further progress of the infection which can lead to severe consequences including death and hence the medical practitioner will usually take samples of the infecting microorganism for testing and start the patient on a broad spectrum antibiotic while waiting for the test results. The use of an antibiotic that is not effective against the infecting organism, however, can actually cause an increase in the growth of the infecting organism as stated.

Further, complications from the use of antibiotics can result from microorganisms developing resistance to the antibiotic. Microorganisms can develop resistance to antibiotics by exposure to subinhibitory levels of the antibiotic which subinhibitory levels allows the growth of any bacteria present that have only marginal susceptibility. Once the resistant strains proliferate, they become the dominant organism causing infection. Though not as common, strains of bacteria have been know to develop resistance to antimicrobial compositions of matter used for sanitizing and disinfecting inanimate surfaces and objects. The overuse and incorrect use of antibiotics in recent years has led to the emergence of bacteria that are resistant to all known antibiotics and present a severe health threat throughout the world. These organisms include but are not limited to antibiotic resistant tuberculosis, methicillin resistant Staphylococcus aureus and vancomycin resistant enterococci. While new antibiotics are continuously developed to deal with this problem it is recognized that the use of compounds such as those found in antibiotic compositions that interfere with normal biochemical mechanisms of growth and proliferation of microorganisms is likely to ultimately lead to the development of strains of bacteria resistant to the new compounds as well.

Hence, there is a serious and pressing need for the development of medications and methods of treatment of infections by bacteria, yeast, mold, rickettsia, viruses and the like that do not have the limitations and side effects observed with antibiotics.

Compositions of matter that kill microorganisms by direct action on the cell wall, referred to as cell lysis, are broadly known and are referred to as biocidal agents. These agents are used to eliminate microorganisms from various surfaces and materials including the surface of the body. Biocidal agents are not capable of circulating through the blood stream and permeating tissues and hence must be applied directly to the offending microorganisms.

Those skilled in the art recognize many biocidal compositions which employ a variety of substances as the active agent including, for example, quaternary ammonium compounds, halogens, fatty acids, anionic surfactants, organic acids, and sulfated and sulfonated aliphatic acids. For example, U.S. Pat. No. 5,143,720 to Lopes discloses mixtures of anionic surfactants and organic acids for use as mouthwash and as bactericides for food and food processing equipment. U.S. Pat. No. 4,404,040 to Wang discloses sanitizing concentrate compositions comprising an aliphatic short chain fatty acid, a hydrotrope or solubilizer for the fatty acid and an acid to produce a pH between 2 and 5 when diluted with water for use in food processing systems. U.S. Pat. No. 4,715,980 to Lopes, et al. discloses sanitizing compositions comprising a dicarboxylic acid and an acidic component that produces a pH below about 5 when diluted with water. U.S. Pat. No. 3,867,300 to Karabinos, et al. discloses bactericidal compositions containing a monocarboxylic fatty acid is protonated making the acid hydrophobic.

While the protonated and hence hydrophobic form of fatty acids is far more biocidal than the unprotonated, hydrophilic form, the hydrophobic form is insoluble in water. The use of a hydrotrope to solubilize the hydrophobic form of fatty acids allows them to remain in solution at a pH below 5.0. It is the use of the protonated form of fatty acids in the presence of suitable hydrotropes that allows complete elimination of microorganisms from internal body spaces or organs in animals and man, which elimination results in the cure or arrest of the associated disease state.

However, as is known to those skilled in the art to which the present invention pertains, the internal organs and spaces of the body of man or animals ordinarily secrete fluids rich in protein and inorganic ions that act to maintain the pH of that tissue or space between about 7.0 to about 7.8. The only tissue or space in the animal body that has a pH below 5.0 is the stomach. The contents of the stomach are emptied into the small intestine and in the first few centimeters of the small intestine secretion from the pancreas acts to raise the pH to 6.5 or above.

There are further complicating aspects of biology that limit the use of biocidal compositions in the internal spaces and organs. The proteins, glycoproteins, lipoproteins, lipids and phospholipids and the like that are secreted from many tissues will act to nourish and harbor microorganisms from direct attack by biocidal compositions of matter. It is a critical aspect of antibiotics that they are able to penetrate most tissues and secretions of the body and hence enter the cell body of the offending microorganism to stop growth of that organism.

Hence the use of fatty acid-based biocidal compositions in the spaces and organs of the body of man and animals to eliminate disease caused by microorganisms will have very limited efficacy unless the pH of the composition is maintained below about 5.0 and, preferably, below about 4.5 by the inclusion of an appropriate organic acid and unless a suitable surfactant is used to expose the microorganism to the biocidal action of the fatty acid.

It has long been recognized that biocidal compositions of matter employing fatty acids can be used to kill microorganisms on the outside of the body and on inanimate surfaces. It is nowhere mentioned in the art, however, nor has it been recognized nor is it readily apparent that these compositions of matter can be used in the internal spaces and organs of the body of man and animals at pH above about 5.0 to treat disease by the elimination of microorganisms.

Fatty acid based biocides are known in the art to be employed in the treatment of Helicobacter pylori infections of the stomach. See, inter alia, Wider U.S. Pat. No. 6,071,761, the disclosure of which is hereby incorporated by reference. The stomach as described above, however, has a pH below 5.0 and the lining of the stomach is known to be able to tolerate low pH conditions without any damage or pathologic changes. Hence it is not readily apparent from this use nor is it suggested in any prior art that acidic compositions of matter employing fatty acids held in solution by appropriate hydrotropes can be tolerated or used in other areas of the body of man or animals. It is to this to which the present invention is directed.

SUMMARY OF THE INVENTION

The composition of the present invention meets the need for elimination of pathogenic organisms from the internal spaces or organs of animals and humans by direct contact with bactericidal and fungicidal agents, avoiding the use of antibiotics. Use of low levels of organic acid in the composition allows the fatty acid(s) to remain protonated but does not cause damage to the body tissues.

In accordance with the present invention there is provided a biocidal or antimicrobial composition, based on USP or food grade components for the treatment of microbial infections of the body spaces and organs of man or animals normally that normally have a pH of 5.0 and above, comprising:

(a) an antimicrobial active agent, (b) a hydrotrope or solubilizer, and (c) a hydrotrope compatible acid.

The composition may be in concentrate or a use solution. As a use solution, the concentrate is admixed with deionized, pyrogen-free water and may be rendered isotonic to body fluids by the addition of the appropriate amount of sodium chloride (NaCl).

The use composition hereof has a pH ranging from about 1.0 to about 5.0 and, preferably ranges from about pH 2.5 to about pH 4.0.

The composition hereof is administered as a liquid either orally or through a suitable delivery system, such as a catheter, an enema tube, needle or the like. Similarly, the composition may be administered as a solid in tablet or encapsulated form.

For a more complete understanding of the present invention, reference is made to the following detailed description and accompanying examples.

DESCRIPTION OF THE PREFERRED EMBODIMENT

The present invention provides a composition and method for preventing and treating infection and disease causing microorganisms. As a concentrate, the composition hereof, generally, comprises:

(a) an antimicrobial active agent, (b) a hydrotrope or solubilizer, and (c) a hydrotrope compatible acid.

Optionally, a vehicle or extender may be used herein.

As a use solution, the concentrate is admixed with deionized, pyrogen-free water and may be made isotonic to body fluids by the addition of the appropriate amount of sodium chloride (NaCl). Similarly, and as discussed below, the composition may be administered in solid form, as well.

The use composition has a pH ranging from about 1.0 to about 5.0 and, preferably, pH 2.5 to about pH 4.0.

The Antimicrobial Active Agent

The antimicrobial active agent herein is one or more aliphatic or aromatic fatty acids either saturated or unsaturated, preferably, saturated, having from 6 to 20 carbon atoms and, preferably, from 8 to 12 carbon atoms. The fatty acid may be linear, branched or cyclic. Preferably, the fatty acid employed is food grade, linear, saturated and unsubstituted fatty acid. Representative of the fatty acids contemplated for use herein include caproic acid, caprylic acid, capric acid and lauric acid, as well as mixtures thereof. Preferably the fatty acid is a mixture of caproic and caprylic acids.

The Solubilizer

A solubilizing agent or stabilizer is employed to enhance the stability and hence the antimicrobial activity of the fatty acids. The use of fatty acids in the protonated state requires the presence of a solubilizing agent to dissolve the fatty acids in aqueous solution and to disrupt protective secretions from both the animal body and the microorganisms.

The antimicrobial action of short chain fatty acids is significantly greater in the protonated state as represented by R—COOH. Undissociated fatty acids have negligible solubility in water and the present invention employs a surfactant hydrotrope, coupler or solubilizer to bring the fatty acids into aqueous solution. Hydrotropes or solubilizers for fatty acids are well known in the art. The preferred solubilizer is non-toxic and retains fatty acids in an aqueous or isotonic use solution. Preferred solubilizers for use in the present invention included anionic surfactants such as alkylphosphates or phosphonates, sugar esters and alkyl glycosides, alkyl sulfates and alkane sulfonates, alpha olefin sulfonates, linear alkyl benzene or napthalene sulfonates, secondary alkane sulfonates, alkyl ether sulfates or sulfonates and dialkylsulfosuccinic acid esters. The choice of solubilizer is dictated by the risk of toxicity to man or animals. The preferred solubilizer is sodium lauryl sulfate.

Hydrotrope Compatible Acids

The present composition requires the presence of a hydrotrope compatible acid in sufficient concentration to provide a pH in the range of about 1.0 to about 5.0, and preferably from about 2.5 to about 4.0 in the use solution. The preferred acid should be compatible with product stability and most specifically not cause the chemical degradation of the hydrotrope. The acid used herein is generally a weak, organic acid such as, for example, citric acid, acetic acid, fumaric acid, maleic acid and the like as well as mixtures thereof.

Mineral acids will produce the same effect and may be used but the organic acids are preferred when sulfated or sulfonated hydrotropes are used due to instability in mineral acids. Citric acid is the preferred acid in the present invention.

Additionally, the use of citric acid provides added antimicrobial effects since citric acid is known to be biocidal.

The present composition when deployed as a liquid may be either a concentrated solution for dilution into a suitable vehicle or a ready to use solution. The present composition, generally, comprises, as a concentrate from 0.1 to 50% by weight of the fatty acid from 0.2 to 40% by weight of the hydrotrope and from about 0.1 to about 10% by weight of the organic acid, based on the total weight of the composition.

As a use solution, the vehicle is usually water or normal saline and the concentrate is present in amount ranging of from about 10 to about 5000 ppm of the fatty acid; from about 20 to about 4000 ppm of the hydrotrope and from about 10 to about 1000 ppm of the organic acid.

As noted, the composition may be disposed or associated with a delivery system such as, a catheter, a needle or an enema delivery device.

The present invention may be encapsulated or incorporated into other solid forms such as time release capsules and the like known in the medicinal arts.

Coating tablets or capsules with polymeric materials such as ethylcellulose, cellulose acetate phthalate copolymer, polysaccharide and the like (see, inter alia, U.S. Pat. No. 5,811,388) delays breakdown of the capsules or tablets until the tablet or capsule is past the stomach and upper gastrointestinal tract, thus, allowing the pH to remain below 5.0.

USE APPLICATIONS

It is contemplated that the composition hereof be used for the treatment of infections of the "internal spaces" of the body of a human or animal. The term "internal spaces" is meant to include, for example, the thorax, abdomen, gastrointestinaltract, urinary bladder, vagina, nasal sinuses, external auditory canal, urethra, and the like.

It is also contemplated that the present composition be used for the elimination of microorganisms from exposed body tissues that normally are not exposed, such as the skin and underlying structure exposed by trauma or incision for or during surgery, or because of the introduction of surgical instruments or other such devices, such as vascular catheters and the like.

Similarly, the present composition may be used where infection is encountered. Thus, for example, the composition hereof can be used as an adjunct to peritoneal dialysis where there is a risk of infection of the abdominal cavity, which is commonly referred to as peritonitis in the medical arts.

Though peritoneal infection is not common in long term maintenance, peritoneal dialysis is encountered every two to three years and can cause serious complications, including death.

During peritoneal dialysis, a hypertonic dialysis fluid is infused into the abdominal cavity and allowed to remain there for several hours after which it is drained and discarded. Peritoneal dialysis involves the use of a hypertonic dialysis fluid which is sterile and pyrogen free and is introduced into the abdominal cavity through a transcutaneous catheter.

As is known to those skilled in the art to which the present invention pertains, the use of transcutaneous devices has the risk of contamination with microorganisms and the introduction of these organisms into the interior spaces of the body. Introduction of microorganisms into the interior spaces of the body frequently leads to growth and proliferation of those organisms causing disease.

Although every effort is made to prevent the introduction of microorganisms into the abdominal cavity during peritoneal dialysis, it happens despite efforts to the contrary. Infections of the peritoneal cavity are serious and can be life threatening.

Introduction of the antimicrobial wash or use solution hereof into the abdominal cavity either separately or in the normal dialysis fluid provides a means of preventing or eliminating infection.

It is to be recognized that the composition hereof is also useful in treating infections of the abdominal cavity caused by factors other than peritoneal dialysis, including, but not limited to, trauma, surgery, perforated bowel, burst appendix, immune deficiency and the like. Furthermore, the present composition may be used to prevent or eliminate contamination of a site by microorganisms at a break in the epidermis (skin) of a man or an animal. The break can lead to the introduction of microorganisms into the tissues surrounding the site of entry or to internal body spaces or organs and result in infection and disease.

As noted above, infection is a potential complication of trauma, surgery, catheter introduction into body spaces or vascular structures and the like. While there are number of products available for preventing microbial growth at the site of entry or disruption of the epidermis, many of these products are based on conventional antibiotics or halogen compounds, specifically iodine and have proven to cause irritation of the skin following prolonged exposure or the development of antibiotic resistant microorganisms. Further, these products are not appropriate for introduction into the internal spaces of the body, including the subcutaneous tissues which are exposed following incisions during surgical procedures.

The present composition can be sprayed onto the skin about five minutes prior to surgical incision and wiped off and the application repeated two more times to eliminate all superficial microorganisms. The composition can also be sprayed into surgical incisions prior to closure of the incision to eliminate any microorganisms introduced into the wound or underlying body space or tissue. Likewise, it can be sprayed into wounds caused by injury from accidental trauma or laceration.

It is well known that the lower gastrointestinal tract of man and animals harbors a rich population of microorganisms, including aerobic, microaerophilic and nonaerobic Gram negative and positive bacteria and fungus. There have been over 400 different species of microorganisms identified in the colon of normal adult humans. The colonic flora is viewed as being essential to normal health and well being and the relative amounts of the various species of flora produces a balance that is critical to normal function. The present composition can be used to treat infection caused by microorganisms in the gastrointestinal tract.

It is well known, also, that imbalance in the normal flora or introduction of pathogenic organisms such as Salmonella or enteropathogenic *E. coli* into the GI tract can lead to discomfort and disease ranging from flatulence to life threatening diarrhea and chronic, hemolytic uremia. Further, it is suspected that microorganisms in the colon contribute to a number of disease entities such as inflammatory bowel disease, hypertension, psychiatric disturbance, diabetes, etc. Elimination of the diverse flora of the lower GI tract is difficult and requires prolonged use of one or more broad spectrum antibiotics which can take days to have an effect, allowing progression of the pathologic changes associated with infection. The present invention alleviates these problems typically associated with antibiotics.

The present composition may also be used a nasal spray for the elimination of both fungal or bacterial growth in the nasal sinuses. Fungal growth in the nasal sinuses has been identified in a high percentage of persons having chronic sinusitis and is believed to be the causative agent in producing chronic inflammation of the sinuses. Spraying can be achieved through any device, such as an atomizer spray device or the like.

For a more complete understanding of the present invention reference is made to the following non-limiting illustrative examples. In the examples all parts are by weight absent contrary indications.

EXAMPLE I

This example illustrates the preparation of an antimicrobial composition in accordance herewith.

Into a suitable sterile vessel equipped with stirring is added to pyrogen-free, deionized water, at ambient conditions, the following USP ingredients:

| Ingredient | Amount, PPM |
|---|---|
| Caprylic acid | 300 |
| Capric acid | 200 |
| Sodium lauryl sulfate | 500 |
| Citric acid | 500 |
| NaCl | 900 |

The resulting composition is sterile and pyrogen free and has a pH of 3.5 and is isotonic to normal body fluids.

This composition has antimicrobial activity against a broad spectrum of microorganisms, including Gram negative and positive bacteria, bacterial spore forms, bacterial L forms, fungi and the like.

EXAMPLE II

This example illustrates the antimicrobial activity of the composition of the present invention.

To illustrate the resistance of the present compsition to microorganisms, the composition of Example I is tested for antimicrobial activity against several clinical isolates of antibiotic resistant bacteria, including Vancomycin resistant enterococci (VRE), multi-drug resistant *Pseudomonas aeruginosa* and Methicillin resistant Staphylococcus aureus (MRSA).

A total of 150 clinical isolates of MRSA, VRE, and multi-drug resistant *Pseudomonas aeruginosa* are evaluated. Microdilution susceptibility is performed according to the National Committee for Clinical Laboratory Standard guidelines. Mueller-Hinton broth supplemented with calcium (25 mg/L) and magnesium (12.5 mg/L) (SMHB) is used for microdilution susceptibility testing. Hydrochloric acid (0.1 mM) is used to adjust the pH of the broth to approximately 4.5. Quality control strains are also tested with each experiment.

The lowest concentration of antibiotic with no growth is the minimum inhibitory concentration (MIC).

| | MIC (ppm/ml) |
|---|---|
| VR *E. faecium*: | |
| 7425 | 31.2 |
| 12867 | 62.5 |
| 13202 | 62.5 |
| 13204 | 62.5 |
| 6672 | 62.5 |
| 6549 | 62.5 |
| 6886 | 62.5 |
| 13285 | 62.5 |
| 7399 | 62.5 |
| 6548 | 62.5 |
| 16306 | 62.5 |
| 16307 | 125 |
| 16308 | 62.5 |
| 16309 | 62.5 |
| 16310 | 62.5 |
| 16311 | 62.5 |
| 16312 | 62.5 |
| 16313 | 62.5 |
| 16314 | 62.5 |
| 16315 | 62.5 |
| 16316 | 62.5 |
| 16319 | 62.5 |
| 16320 | 62.5 |
| 16321 | 62.5 |
| 16322 | 62.5 |
| 16324 | 62.5 |
| 15666 | 62.5 |
| 15684 | 62.5 |
| 16055 | 62.5 |
| 15692 | 62.5 |
| VR *E. faecalis*: | |
| 16317 | 31.2 |
| 15667 | 62.5 |
| 14225 | 31.2 |
| 14231 | 62.5 |
| 12905 | 62.5 |
| 13078 | 62.5 |
| 13132 | 62.5 |
| 13134 | 62.5 |
| 13197 | 31.2 |
| 13307 | 62.5 |
| 13422 | 62.5 |
| 13548 | 62.5 |
| 13563 | 62.5 |
| 13577 | 62.5 |
| 13578 | 62.5 |
| 13579 | 31.2 |
| 13688 | 31.2 |
| 13962 | 62.5 |
| 14067 | 62.5 |
| *P. aeruginosa*: | |
| 11374 | 1000 |
| 11956 | 1000 |
| 11979 | 1000 |
| 11987 | 1000 |
| 11943 | 1000 |
| 11911 | 1000 |

| | |
|---|---|
| 10962 | 1000 |
| 11913 | 1000 |
| 12023 | 1000 |
| 10756 | 1000 |
| 14928 | 1000 |
| 14929 | >1000 |
| 14932 | 1000 |
| 14941 | 1000 |
| 14946 | 1000 |
| 14971 | 1000 |
| 14939 | 1000 |
| 14972 | 1000 |
| 15034 | >1000 |
| 15035 | 1000 |
| 15039 | 1000 |
| 15046 | 1000 |
| 15050 | 1000 |
| 15051 | 1000 |
| 15107 | 1000 |
| 15108 | 1000 |
| 15109 | 1000 |
| 15164 | 1000 |
| 15165 | 1000 |
| 15196 | 1000 |
| 15197 | 1000 |
| 15218 | 1000 |
| 15220 | 1000 |
| 15221 | 1000 |
| 15222 | 1000 |
| 15225 | 1000 |
| 15228 | 500 |
| 15229 | 1000 |
| 15230 | 1000 |
| 15245 | 1000 |
| 15246 | 1000 |
| 15300 | 1000 |
| 15309 | 1000 |
| 15310 | 1000 |
| 15311 | 1000 |
| 15312 | 1000 |
| 15313 | 1000 |
| 15314 | 1000 |
| 15321 | 1000 |
| 15425 | 1000 |
| MRSA: | |
| 14377 | 62.5 |
| 14384 | 62.5 |
| 12398 | 31.2 |
| 12400 | 62.5 |
| 12557 | 31.2 |
| 12627 | 62.5 |
| 12723 | 31.2 |
| 12757 | 62.5 |
| 12601 | 31.2 |
| 12641 | 31.2 |
| 12722 | 62.5 |
| 12736 | 31.2 |
| 12758 | 62.5 |
| 12759 | 62.5 |
| 12765 | 31.2 |
| 12813 | 31.2 |
| 12821 | 31.2 |
| 12863 | 31.2 |
| 12882 | 31.2 |
| 12909 | 31.2 |
| 12911 | 62.5 |
| 12912 | 31.2 |
| 12960 | 62.5 |
| 13049 | 62.5 |
| 14376 | 62.5 |
| 14384 | 62.5 |
| 14444 | 62.5 |
| 14445 | 62.5 |
| 14511 | 62.5 |
| 14539 | 31.2 |
| 14622 | 31.2 |
| 14670 | 31.2 |
| 14821 | 31.3 |
| 14855 | 31.2 |
| 14899 | 31.2 |
| 14900 | 62.5 |
| 14901 | 31.2 |
| 14902 | 31.2 |
| 14943 | 62.5 |
| 15043 | 62.3 |
| 15193 | 31.2 |
| 15207 | 31.2 |
| 15426 | 31.2 |
| 15543 | 62.5 |
| 15549 | 31.2 |
| 15552 | 31.2 |
| 15562 | 31.2 |
| VISA: | |
| 14358 | 62.5 |
| 14342 | 62.5 |
| QC: | |
| MRSA 29213 | 31.2 |
| VRE 29212 | 62.5 |
| PA 27853 | 1000 |

| | MIC50 (ppm/ml) | MIC90 (ppm/ml) | MIC (range) (ppm/ml) |
|---|---|---|---|
| VRE | 62.5 | 62.5 | 31.2–125 |
| MRSA | 31.2 | 62.5 | 31.2–62.5 |
| PA | 1000 | 1000 | 500–1000 |

MRSA = methicillin-resistant *Staphylococcus aureus*
VRE = vancomycin-resistant *enterococci*
PA = *Pseudomonas aeruginosa*

EXAMPLE III

This example shows the resistance of the present invention to microorganisms.

Microorganisms can develop resistance to antibiotics by exposure to subinhibitory levels of the antibiotic which subinhibitory levels allows the growth of any bacteria present that have only marginal susceptibility. Once the resistant strains proliferate, they become the dominant organism causing infection. Though not as common, strains of bacteria have been known to develop resistance to antimicrobial compositions used for sanitizing and disinfecting inanimate surfaces and objects.

The composition of Example I is tested for the development of resistance to the composition in clinical isolates of enterococci, *S. aureus* and *P. aeruginosa*.

To determine if resistance develops after exposure to subinhibitory concentrations of the composition isolates of each enterococci, *S. aureus* and *P. aeruginosa* are selected for resistance studies. Minimum Inhibitory Concentration (MIC) of the composition is determined for each isolate by broth microdilution Bacteria (106 CFU/ml) are exposed to the subinhibitory concentration (½×MIC). Bacteria (106CFU/ml) are then passed daily to fresh broth containing ½×MIC. Following 5 passages, the MIC of the bacteria was evaluated by broth microdilution. This procedure is repeated for 30 passages or until an MIC increase of 2–4 fold is observed.

There is no observed change in the MIC after 30 passages indicating that the compositionndoes not lead to the development of resistant microorganisms.

EXAMPLE IV

To test the present compsition for tissue tolerance a series of tests are carried out to investigate the potential of the composition of Example I to cause discomfort or inflammation in the abdominal cavity or nasal passages, both body spaces being very sensitive to irritation and inflammation.

Seven normal rats are injected intraperitoneally with 0.5 ml of composition of Example I to test for tolerance of the product in the abdominal cavity. Seven control rats are injected with normal saline. There is no indication of discomfort in any of the rats. One hour following injection, the animals are sacrificed and the peritoneal membranes and organs examined. Post mortem examination indicates no inflammatory reaction, hyperemia or collection of fluid.

EXAMPLE V

This example illustrates the use of the present composition as an adjunct to peritoneal dialysis to prevent or eliminate infection in the abdominal cavity. One liter of the composition of Example I is infused into the abdominal cavity of a human and allowed to remain there for 5 to 20 minutes after which time it is drained an discarded.

The volume of antimicrobial infused depends on the patient size, but should be enough to reach all surfaces in the abdominal cavity. Thus, usually 0.5 to 1.0 liter is ordinarily sufficient for infusion into the abdominal cavity of a human.

The composition here is also useful in treating infections of the abdominal cavity caused by factors other than peritoneal dialysis, including, but not limited to, trauma, surgery, perforated bowel, burst appendix, immune deficiency and the like.

EXAMPLE VI

This example illustrates the use of the present invention as a nasal spray. Two sprays in each nasal orifice three times a day is taken and allowed to remain for five to ten minutes before blowing the nose to clear remaining product. The product is used for three days. Spraying of the composition daily for a period of three days causes no irritation or rhinitis or any other perceptible discomfort.

EXAMPLE VII

This example illustrates the preparation of an antimicrobial composition in accordance herewith for gastrointestinal use.

Into a suitable sterile vessel equipped with an appropriate mixing device, is added at ambient conditions, the following USP ingredients:

| Ingredient | Amount, PPM |
|---|---|
| Sodium caprylate | 120 |
| Sodium caprate | 180 |
| Sodium lauryl sulfate | 300 |
| Citric acid | 300 |

The resulting composition is encapsulated into tablet form for oral administration.

The tablets or capsules are coated to prevent dissolution of the product in the stomach or upper gastrointestinal tract. The composition is taken 3 times a day until the pH of the stool is below 5.0, after which the tablet is taken for two more days.

EXAMPLE VIII

This example illustrates the use of the present invention in treating achlorhydria.

The secretion of hydrochloric acid by the cells lining the stomach normally kills most microorganisms presented to the lumen of the stomach. Failure of the stomach to secrete hydrochloric acid is referred to in the medical arts as achlorhydria and is associated with bacterial and fungal growth in the stomach which can lead to discomfort and disease.

The composition of Example VIII is taken orally in tablet form to eliminate bacterial or fungal growth associates with achlorhydria. 900 mg of the concentrate is taken orally in uncoated encapsulated form following an overnight fast and, then, every four hours following with 50 cc of water.

What is claimed is:

1. A method for eliminating microbial contamination caused by bacteria, bacterial spore forms, antibiotic resistant bacteria and fungi in the internal spaces and tissues of the body having a pH greater than 5.0 of an individual in need thereof, comprising:
    contacting the internal space or tissue to a bacterial arresting amount of a liquid composition consisting essentially of:
    a) a microbial arresting agent selected from the group consisting of an aliphatic fatty acid, an aromatic fatty acid or mixtures thereof, the fatty acid having from about 6 to about 20 carbon atoms;
    b) a hydrotrope;
    c) a hydrotrope compatible acid; and
    d) transport medium consisting essentially of deionized, pyrogen free water.

2. The method of claim 1 wherein in the composition the fatty acid is a linear unsubetituted saturated fatty acid.

3. The method of claim 1 wherein the fatty acid is selected from the group consisting of caproic acid, caprylic acid, capric acid, lauric acid and mixtures thereof.

4. The method of claim 1 wherein in the composition the hydrotrope is an anionic surfactant.

5. The method of claim 4 wherein the anionic surfactant is selected from the group consisting of alkylphosphates, alkyl phosphonates, sugar esters, alkyl glycosides, alkyl sulfates alkane sulfonates, alpha olefin sulfonates, linear alkyl benzene, linear alkyl, naphthalene sulfonates, secondary alkane sulfonates, alkyl ether sulfates, alkyl ether sulfonates and dialkylsulfosuccinic acid esters, the salts thereof and mixtures thereof.

6. The method of claim 5 wherein the anionic surfactant is sodium lauryl sulfate.

7. The method of claim 1 wherein the hydrotrope compatible acid is selected from the group consisting of citric acid, acetic acid, fumaric acid, maleic acid, and mixtures thereof.

8. The method of claim 1 wherein:
    a) the antimicrobial compound comprises from about 0.1% to about 15%, by weight, based on the total weight;
    b) the hydrotrope comprises from about 0.1% to about 30%, by weight, based on the total weight;
    c) the hydrotrope compatible acid comprises from about 0.1% to about 50%, by weight, based on the total weight; and
    d) the balance is a transport medium vehicle for the composition.

9. Method of claim 7 wherein the transport medium is an isotonic solution of salts in deionized, pyrogen free water.

10. Method of claims 1 wherein the transport medium is an isotonic solution of a sugar in pyrogen free water.

11. Method of claim 1 wherein the transport medium is an isotonic solution of a sugar and salt in deionized, pyrogen free water.

12. The method of claim 1 wherein the internal space is the space exposed during surgical intrusion and the internal space is contacted by washing.

13. The method of claim 1 wherein the internal space is the space exposed by an open wound.

14. The method of claim 1 wherein the internal space is the nasal passages of the body.

15. A method of claim 1 wherein the internal space is the vaginal canal.

16. A method of claim 1 wherein the internal space is the urinary bladder and urinary tract.

17. The method of claim 1 wherein the internal space is the abdominal cavity following introduction of the contents of the gastrointestinal tract thereinto.

18. A method of claim 1 wherein the internal space is the colon.

19. The method of claim 1 wherein the composition is a concentrate.

20. A microbial contamination eliminating delivery system which comprises:

a) a container for temporarily storing a liquid composition, b) a delivery tube for delivering the composition in the container to a body cavity, the delivery tube being in fluid communication with the content of the container, and c) a quantity of liquid contained within the container for delivery into a body passage, the body passage being at a pH greater than 5.0, the liquid consisting essentially of:

(i) a microbial arresting agent selected from the group consisting of an aliphatic fatty acid, an aromatic fatty acid, and mixtures thereof the fatty acid having from about 6 to about 20 carbon atoms;

(ii) a hydrotrope;

(iii) a hydrotrope compatible acid; and (iv) transport medium consisting essentially of deionized. pyrogen free water.

* * * * *